(12) United States Patent
Ingenhoven et al.

(10) Patent No.: US 7,153,405 B2
(45) Date of Patent: Dec. 26, 2006

(54) CASSETTE, SYSTEM, AND 2-D GEL ELECTROPHORESIS METHOD FOR SEPARATING MOLECULES

(75) Inventors: Nikolaus Ingenhoven, Männedorf (CH); Remo Hoechli, Dürnten (CH); Marcel Rutishauser, Wolfhausen (CH); Anton Posch, Grafing (DE)

(73) Assignee: Tecan Trading AG, Männedorf (CH)

( * ) Notice: Subject to any disclaimer, the term of this patent is extended or adjusted under 35 U.S.C. 154(b) by 660 days.

(21) Appl. No.: 10/409,920

(22) Filed: Apr. 9, 2003

(65) Prior Publication Data
US 2004/0045829 A1 Mar. 11, 2004

Related U.S. Application Data

(60) Provisional application No. 60/377,326, filed on May 2, 2002.

(30) Foreign Application Priority Data
Apr. 12, 2002 (CH) .................................... 0611/02

(51) Int. Cl.
*B01D 57/02* (2006.01)
*G01N 27/26* (2006.01)

(52) U.S. Cl. ...................... 204/466; 204/456; 204/462; 204/610; 204/613; 204/616; 204/623; 422/50

(58) Field of Classification Search ............... 204/456, 204/459, 462, 466, 548, 606, 608, 610, 613, 204/616, 620, 621, 623, 467; 422/50
See application file for complete search history.

(56) References Cited

U.S. PATENT DOCUMENTS 4,999,340 A * 3/1991 Hoffman et al. ............. 514/23

| | | | |
|---|---|---|---|
| 5,228,971 A | 7/1993 | Brumley, Jr. et al. | 204/299 |
| 5,338,426 A | 8/1994 | Shigeura et al. | 204/299 |
| 5,627,022 A | 5/1997 | Renfrew et al. | 435/4 |
| 6,113,766 A | 9/2000 | Steiner et al. | 204/606 |
| 6,156,182 A | 12/2000 | Olech et al. | 204/610 |
| 6,179,980 B1 * | 1/2001 | Aksberg | 204/616 |
| 2001/0037940 A1 * | 11/2001 | Shih et al. | 204/466 |

FOREIGN PATENT DOCUMENTS

| WO | PCT/US00/11547 | 4/2000 |
|---|---|---|
| WO | WO 00/65336 | 11/2000 |

* cited by examiner

*Primary Examiner*—Nam Nguyen
*Assistant Examiner*—Anthony Fick
(74) *Attorney, Agent, or Firm*—Notaro & Michalos P.C.

(57) ABSTRACT

A gel electrophoresis cassette (33) is disclosed which includes two plates (34, 35) and at least one seal (36) which separates these plates. The seal (36) is annular; it may be positioned essentially in the region of the outer edge of the plates (34, 35). For performing an electrophoresis in a second dimension following an isoelectric focusing in an first dimension, one of the plates (34, 35) includes a recess (37) for inserting a strip holder (1) having a base plate (4), which has a carrier surface (2) on which an IEF strip (3) is accommodated. The base plate (4) includes at least one stop (5) offset to a lower level in relation to the carrier surface (2) and a sealing surface (6). The strip holder (1) is insertable into this recess (37) in such a way that the stop (5) of the base plate (4) is applied to the outer surface of the plate (34, 35) and the sealing surface (6) presses tightly against the inner surface (38) of the recess (37). In addition, systems and methods for performing a 2-D gel electrophoresis are disclosed.

25 Claims, 6 Drawing Sheets

CASSETTE, SYSTEM, AND 2-D GEL ELECTROPHORESIS METHOD FOR SEPARATING MOLECULES

RELATED APPLICATION DATA

This patent application claims priority of the Swiss patent application No. CH 0611/02 filed on Apr. 12, 2002 and of the U.S. provisional application No. 60/377,326 filed on May 2, 2002. The entire disclosure of the text and the drawings of this US provisional application is incorporated into this regular application by reference.

FIELD OF THE INVENTION

The present invention relates to a gel electrophoresis cassette which includes two plates and at least one seal separating these plates according to the preamble of independent Claim 1; as well as a corresponding system for performing 2-D gel electrophoresis according to the preamble of Claim 8 and a corresponding 2-D gel electrophoresis method according to the preamble of independent Claim 13.

BACKGROUND OF THE INVENTION

More than 25 years ago, O'Farrell [O'Farrell PH. *J. Biol. Chem.* 1975, 250:4007–4021] published a method for high-resolution separation of proteins of the bacteria *Escherichia coli* using two-dimensional polyacrylamide gel electrophoresis (2-D PAGE). In the meantime, this method has been refined and today it is one of the most applied techniques for the analysis and characterization of complex protein mixtures. The application of isoelectric focusing (IEF) as the first step of 2-D PAGE allows the separation of the proteins on the basis of their charge, and may be performed in polyacrylamide gels with or without an immobilized pH gradient [cf. Görg A., Postel W., and Günther S. The current state of 2-dimensional electrophoresis with immobilized pH gradients. *Electrophoresis* 1988, 9:531–546]. In the second step, polyacrylamide gels, which contain sodium dodecyl sulfate (SDS) as an anionic detergent and which are particularly suitable for separating proteins on the basis of their molecular weight, are preferably used. Therefore, 2-D PAGE is capable of separating proteins on the basis of two independent parameters, charge and size.

A device for rehydrating a gel strip and performing an IEF as a first step of a 2-D PAGE is known from U.S. Pat. No. 6,113,766. The device includes a chamber which is suitable both for rehydrating a prefabricated and dried gel strip and for performing the IEF. For this purpose, the gel strip is placed in the chamber in such a way that—gel side down—each of its end regions comes to rest on one electrode in the chamber floor. The chamber is sealable using a cover, which exercises a specific pressure on the gel strip via pressure parts, so that the gel is pressed onto the electrodes. Following the IEF, i.e., the separation of the proteins in a first dimension, the gel strip is removed from the chamber and laid on an SDS-polyacrylamide gel for performing the separation of the proteins in the second dimension. The gel strip may be damaged as this is done, which may endanger the success of the entire 2-D gel electrophoresis. In addition, achieving a pressure which is sufficiently large to ensure the electrical contact for the IEF, but is small enough that the gel is not damaged is extremely difficult and complicated, because the degree of rehydration of the IEF gel additionally influences its volume.

A solution of the first problem described is known from German Patent 198 31 210, in which a practically simultaneous casting of the gel for the first and second dimension in a joint device is disclosed. The IEF gel is only separated from the SDS-PAGE gel by a narrow element, which may be removed after completion of the IEF and thus leaves a space open which may be filled with a contact gel to bring both gels into contact. The SDS-PAGE may be performed after this. This solution has the advantage that the IEF gel strip does not have to be touched or transported at all between the first and second dimension of a 2-D PAGE. However, it is disadvantageous that both gels must be discarded if the IEF is not successful. In addition, it is known that the reproducibility of IEF results is significantly improved if IEF gels of the same batch are used. This would mean that a large number of gels for the first and second dimension would have to be cast at the same time and under the same conditions, which may become very costly.

Another solution of the first problem described is disclosed in U.S. Pat. No. 5,993,627. In a fully automated system for performing 2-D gel electrophoresis, gels for both the first and the second dimension are cast. The system also includes devices for performing the electrophoresis, the subsequent gel staining, and the analysis. The system is based on the production of IEF gels on a "backing material" made of Gelbond®, on the transfer of this gel into a mold for casting the SDS gel, into which a massive electrode Is also cast simultaneously. The system requires multiple robot arms and/or gripping tools for grasping and transporting the gels from one container (IEF chamber) to the other (SDS-PAGE chamber, staining chamber, and scanning bed). The Gelbond® material does improve the stability of the IEF strip, but the method suggested is complicated and costly, and the system is correspondingly expensive.

SUMMARY OF THE INVENTION

The present invention has the object of providing an alternative device which removes or at least minimizes the disadvantages known from the related art. The object is achieved according to a first aspect by the combination of features of independent Claim 1, according to a second aspect by the combination of features of Claim 8, and according to a third aspect by the combination of features of independent Claim 13. Advantageous refinements and additional features of the present invention result from the dependent claims.

BRIEF DESCRIPTION OF THE DRAWINGS

The present invention will now be described in more detail with reference to schematic and exemplary drawings, which are not to restrict the extent of the present invention.

DETAILED DESCRIPTION OF THE INVENTION

Figure 1:
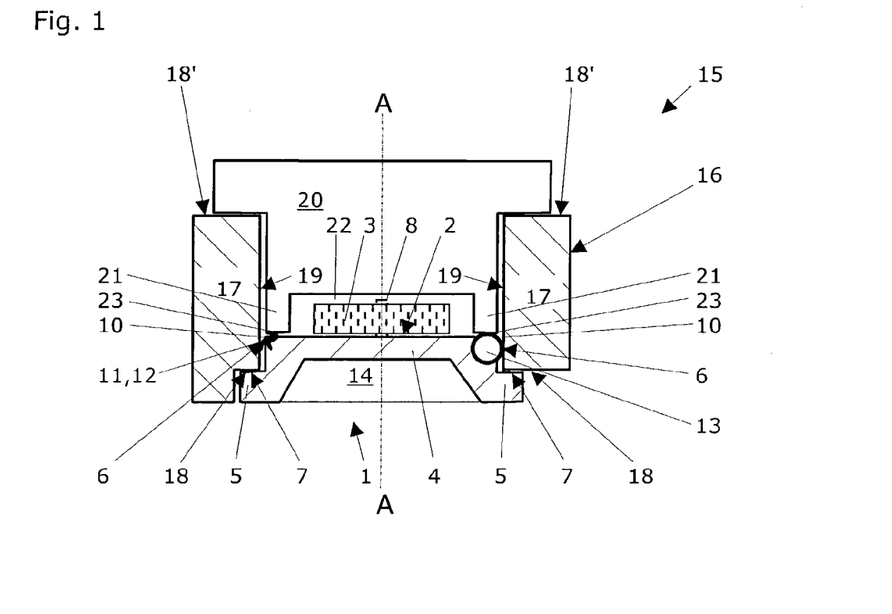
FIG. 1 shows a perpendicular cross-section through a closed IEF chamber having an IEF gel strip inserted.

FIG. 1 shows a strip holder 1 having a base plate 4 which includes a carrier surface 2 for accommodating a gel strip 3 for separating molecules using gel electrophoresis. Base plate 4 includes at least one stop 5, which is offset to a lower level in relation to carrier surface 2, and at least one sealing surface 6. This stop is implemented to be applied to counter surfaces 7 of an electrophoresis chamber, through which the installation depth of strip holder 1, which carries a gel strip 3, into this electrophoresis chamber is determined and the sealing surface 6 ensuring a sealed installation of strip holder 1, which carries a gel strip, into this electrophoresis chamber.

Stop 5 is implemented in one piece with base plate 4 in this case and forms a continuous peripheral stop surface. Alternatively, it may be provided (not shown), that the stop surface is subdivided or replaced by a bow attached to base plate 4 with the same effect. While base plate 4 is preferably manufactured from a chemically inert, electrically insulating material having good thermal conduction properties, such bows may be produced from another material (e.g. from metal) and, for example, be cast into or screwed onto the base plate.

Base plate 4 preferably has one perpendicular pin 8 in the region of each of the two carrier surface ends, which are implemented for the penetrative positioning of gel strip 3. In addition, the base plate may have depressions 9 for accommodating buffer solution outside carrier surface 2 for gel strip 3. Sealing surface 6 may be implemented as a lip seal 11, molded onto outermost, upper edge 10 of the base plate, having one or two sealing lips 12. This lip seal 11 is preferably produced in one piece with strip holder 1 in a two-component injection molding method, sealing lips 12 preferably being produced from a more elastic plastic than strip holder 1. Alternatively to a lip seal which is sprayed on, an O-ring 13 may also be positioned in place of lip seal 11, in this case—depending on the material of the strip holder— O-ring 13 may be laid in a peripheral groove or sprayed onto the strip holder and/or produced together with the strip holder in a two-component injection molding method. Embodiments which favor cost effective mass production of strip holders conceived as consumables are preferred.

As already noted, base plate 4 is preferably manufactured from a chemically inert, electrically insulating material, plastics which are capable of being injection molded being particularly preferred in this case. Base plate 4 is also to have good thermal conduction properties, so that during the rehydration of the IEF gel and, above all, during the IEF gel electrophoresis, the temperature of the gel may be controlled better. For this purpose, the base plate preferably has a lower hollow 14 for accommodating a cooling rib (not shown) of a cooling unit.

Furthermore, FIG. 1 shows a chamber 15 for the isoelectric focusing (IEF) of molecules in gel strips 3. This chamber includes a strip holder 1 and a frame 16 having a peripheral wall 17 and an upper and lower counter surface 18, 18'. Strip holder 1 is inserted into frame 16 in such a way that the at least one stop 5 is applied to counter surface 18 and lower sealing lip 12 presses tightly against an inner surface 19 of wall 17. The chamber also includes a cover 20 to be applied to upper counter surface 18' of frame 16. Cover 20 preferably has a bead in the form of a peripheral rib 21 which projects into chamber 15 and limits inside 22 of the chamber over gel strip 3. At the same time, outermost lower edge 23 of bead 21 is applied to a sealing lip 12 of lip seal 11 to form a seal. Alternatively, lower edge 23 of bead 21 is also applied to an O-ring 13 attached to strip holder 1. The cover is preferably provided with contact pins or other suitable, removable contact means (not shown), so that the circuit, for the safety of the operator, is only closed when chamber 15 is sealed and is automatically interrupted when the chamber is opened.

Figure 2:
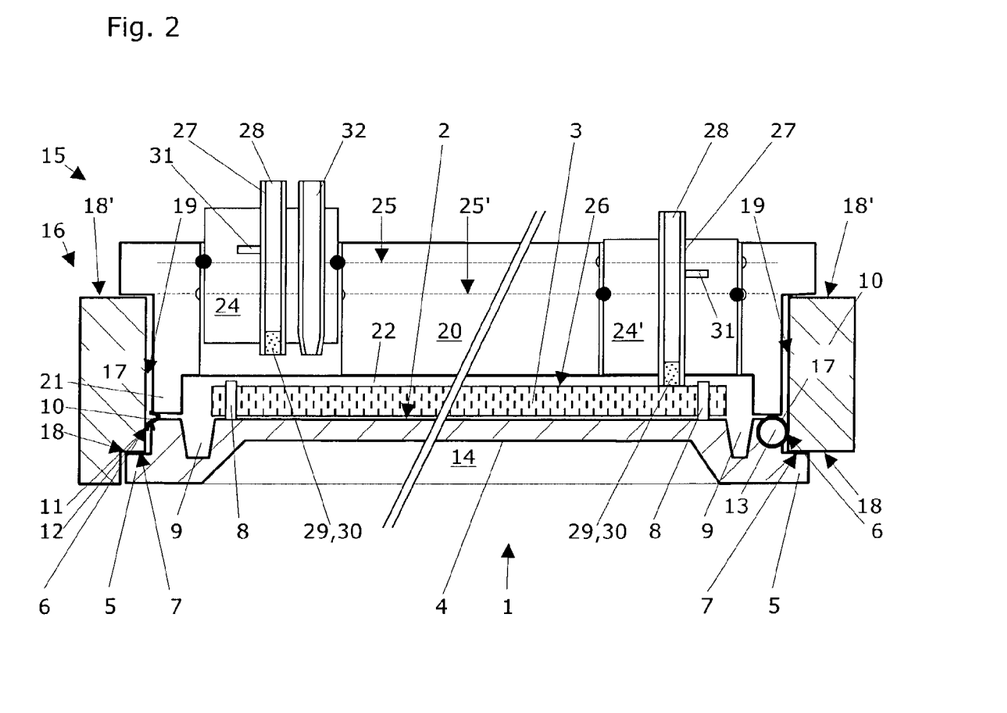
FIG. 2 shows a perpendicular longitudinal section through a closed IEF chamber having a gel strip inserted, along section line A—A in FIG. 1.

FIG. 2 shows a perpendicular longitudinal section through a closed IEF chamber having a gel strip inserted. The section runs along the section line indicated in FIG. 1 with A—A. Two electrode holders 24, 24' may be inserted into cover 20. These electrode holders are preferably implemented so they are insertable into two defined levels 25, 25' and each include an electrode 27, which has limited movability perpendicular to surface 26 of a gel strip 3 lying on carrier surface 2 of strip holder 1. These electrodes 27 are implemented as small tubes made of electrically nonconductive material (e.g. glass, plastic, ceramic) having one open upper opening 28 and have a frit 30 which partially seals lower opening 29. Alternatively, conductive material may also be used for the tubes. Electrodes 27 also have a laterally branching electrical contact 31. The hollow electrodes may be at least partially filled with buffer solution and thus represent an electrically conductive connection between a high voltage control (not shown) and the two poles of a gel strip 3. Frit 30 is a filter, which is permeable to the buffer and to ions or excess proteins migrating to electrodes 27 during the IEF, and which prevents crystallization of these particles on the electrodes due to its permeability. Especially in devices for automated performance of IEF electrophoresis, a reduced rate of contamination and/or simpler cleaning is expected thanks to these electrodes 27. In spite of this permeability, frit 30 represents a flow resistance for the buffer in the tube which is great enough that it may not run out spontaneously due to its hydrostatic pressure.

As an alternative to the open version described, the electrode tubes may be sealed on their upper end except for a supply line (inlet, not shown). An outlet is then positioned in place of laterally branching electrical contact 31. The inlet and outlet are then connected to a circulation system for temperature control and/or filtration of the buffer. The electrical connection to a suitable high voltage control is then also produced via the inlet or outlet.

The first part (first dimension) of a 2-D gel electrophoresis method using strip holder 1 and/or chamber 15 according to the present invention preferably runs as follows:

A dehydrated gel strip 3 is positioned on carrier surface 2 of a strip holder 1.

This strip holder 1 is inserted into a frame 16, having a peripheral wall 17 and an upper and lower counter surface 18, 18', in such a way that the at least one stop 5 is applied to lower counter surface 18 and sealing surface 6 presses tightly against an inner surface 19 of wall 17.

Gel strip 3 inside this chamber 15 is layered with rehydration solution. Alternately, gel strip 3 may be layered with oil before the application of the sample to avoid evaporation losses. In this case, a sample may already be contained in this rehydration solution; if this is not the case, the sample may be applied to the gel strip and/or introduced into the gel strip later (preferably in a strip shape with the chamber open and/or via a sample tube 32 with the chamber closed and the high voltage switched on; cf. below).

The chamber is closed using a cover 20 to be applied to upper counter surface 18' of frame 16 and two electrode holders 24, 24' insertable in this cover 20. In this case, the electrode holders are inserted into an upper level 25, due to which one electrode 27 at a time, which are each restrictedly movable perpendicular to surface 26 of a gel strip 3 lying on the carrier surface 2 of strip holder 1, is positioned at a distance to this surface 26.

After the sample is diffused into the gel, the electrode holders are lowered to a lower level 25', due to which both electrodes 24, 24' come into contact with this surface 26 of gel strip 3.

Gel strip 3 is subjected to electrical high voltage via electrodes 24, 24' until the isoelectric focusing (IEF) of the molecules in the gel has occurred. In this case, the electrical high voltage is preferably generated using a single channel control device, which regulates the electrical current parameters and in addition stores them so they may be called up and, for example, displayed on a display screen.

The application of the sample onto the gel may—according to a first variant of the method according to the present invention—be performed by applying the sample in a strip shape onto gel 3 when chamber 15 is opened. This is preferably performed using a pipettor, which may reproducibly dispense a specific quantity of sample. Chamber 15 is then closed using a cover 20 to be applied to upper counter surface 18' of frame 16 and two electrode holders 24, 24' which are insertable in this cover 20. In this case, the electrode holders are inserted into an upper level 25, due to which one electrode 27 at a time, which are each restrictedly movable perpendicular to surface 26 of a gel strip 3 lying on the carrier surface 2 of strip holder 1, is positioned at a distance to this surface 26, until the sample has diffused into the gel. The restricted movability of the electrodes in the Z direction described may be produced in various ways. Electrodes 27 may be freely guided in the Z direction (perpendicular to the surface of the IEF gel, which lies essentially horizontally), so that they are applied to the IEF gel with their intrinsic weight (including tube, frit, and buffer filling). Electrodes 27 may be adjusted in their Z position using one or more spring elements (not shown) in such a way that they are applied to the IEF gel surface with a defined pressure. The Z movability of the electrodes is therefore restricted on one side by at least one spring element and/or one end stop (both not shown), so that the electrodes may not come into contact with gel surface 26 if electrode holder 24, 24' is inserted in upper level 25. Both variants of the Z movability allow soft but reliable contact with the gel surface, so that the electrical contact for the IEF is ensured without the gel being damaged. Electrode holders 24, 24' are subsequently lowered to a lower level 25', due to which both electrodes 27 come into contact with this surface 26 for performing the IEF.

The application of the sample onto the gel may—according to second variant of the method—be performed by closing chamber 15 using a cover 20 to be applied to upper counter surface 18' of frame 16 and two electrode holders 24, 24' which are insertable in this cover 20, in that the electrode holders are inserted directly into a lower level 25'. In this way, one electrode 27 at a time and at least one sample tube 32, all of which are restrictedly movable perpendicular to surface 26 of a gel strip 3 lying on the carrier surface 2 of strip holder 1 (cf. variant 1), come into contact with this surface 26. Subsequently, the sample is drawn into the gel strips from sample tube 32 while an electrical voltage is applied to the gel.

The performance of this method in an appropriate automatic system (not shown) is especially preferred, in this case, this system may include a working platform for arranging one or more IEF chambers and may be equipped with a cooling device for cooling the IEF chambers. Such a system preferably also includes a robot arm for transferring individual parts of the chamber to and from these IEF chambers and/or SDS-PAGE cassettes, as well as a computer for controlling the robot, a single-channel high voltage control for individual control of the IEF chambers, and a display screen. Using such a system, which preferably also includes a pipettor having multiple channels, the rehydration solution may also be supplied automatically and in a defined quantity, so that no excess rehydration solution must be removed from the chamber.

Figure 3:
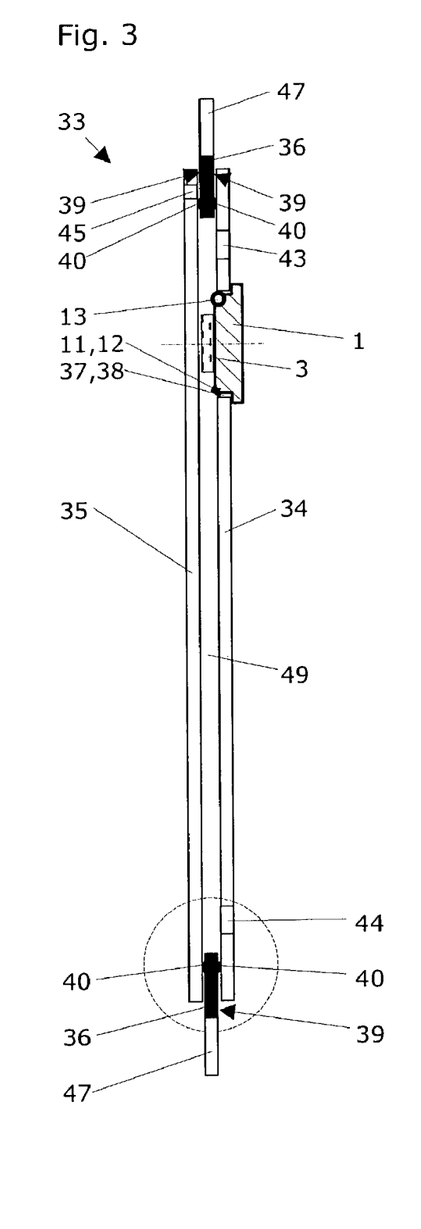
FIG. 3 shows a perpendicular cross-section through an SDS-PAGE cassette having an inserted strip holder and IEF gel, according to a first embodiment.

FIG. 3 shows a perpendicular cross-section through an SDS-PAGE cassette 33 for performing electrophoresis in a second dimension, following the isoelectric focusing, having an inserted strip holder 1 and a IEF gel strip 3. This cassette 33 according to a first embodiment includes two plates 34, 35 and at least one seal 36 separating these plates. A strip holder 1 is inserted into a recess 37 in one of these plates 34 in such a way that the at least one stop 5—preferably set off to a lower level by the dimension of the plate thickness—is applied to the outer surface of plate 34, which acts as a counter surface 7, and sealing surface 6 presses tightly against inner surface 38 of recess 37. In this case, gel strip 3 almost fills up space 49 between plates 34, 35 and carrier surface 2 is essentially flush with the inner surface of front plate 34.

Here, the seal 36 is implemented as an essentially flat, one-piece, annular seal, which is essentially positionable in the region of the outer edge of plates 34, 35, with seal 36 including an annular, peripheral, elastically deformable sealing edge 40 on each of sides 39, which press against the plates. Seal 36 also includes attachment nubs 41, lying in the region outside its sealing edge 40, which are implemented to be snapped into corresponding holes 42 incorporated into both plates 34, 35. At least one of the plates (in this case front plate 34) includes first openings 43, positioned in the region of the space defined inside sealing edge 40, for introducing a gel, buffer, or stain and/or second openings 44 for ventilation or for introducing a gel, buffer, or stain. Front and back plates 34, 35 also include, positioned inside the region of the space covered by seal 36, third openings 45 for introducing a separating medium.

Figure 4:
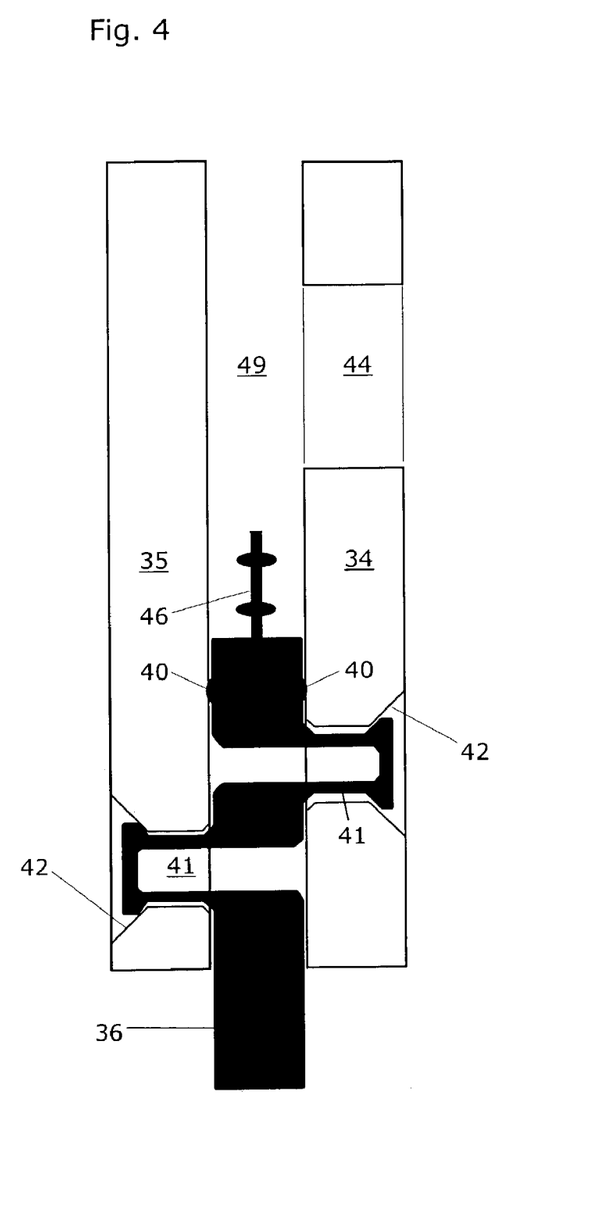
FIG. 4 shows an enlarged detail section (cf. circle in FIG. 3) through the seal of the SDS-PAGE cassette.

FIG. 4 shows an enlarged detail section (corresponding to the circle in FIG. 3) through the seal of an SDS-PAGE cassette 33. Essentially flat seal 36 is essentially positioned in the region of the outer edge of plates 34, 35 and has an annular, peripheral, elastically deformable sealing edge 40 on each of sides 39, which press against the plates 34, 35. Attachment nubs 41, which lie in the region outside their sealing edge 40, are positioned alternating, so that the seal may be removed from the mold easily after the manufacturing process for its production (e.g. injection molding). In spite of this, two attachment nubs 41 are always positioned so near one another that they act like a direct connection between plates 34, 35. When cassette 33 is assembled, the snapping of attachment nubs 41 into holes 42 of plates 34, 35 provided for them has the effect that the three main elements are provisionally held together and seal 36 remains correctly positioned during installation of cassette 33 into a holding device (not shown).

Plates 34, 35 are preferably produced from glass. Seal 36 preferably has an elasticity which essentially corresponds to that of an SDS gel, the toughness of the seal, however, being greater than that of the gel. In order that the SDS gel does not have to be grasped and/or in order that the SDS gel may be handled carefully, seal 36 includes clips 46 to be polymerized into such a gel. These clips preferably have a relief pattern (having a network structure, holes, nubs, and the like), which is suitable for producing intimate contact with the SDS gel. A chemical bond is preferably produced between the gel and the clips of the seal.

Figure 5:
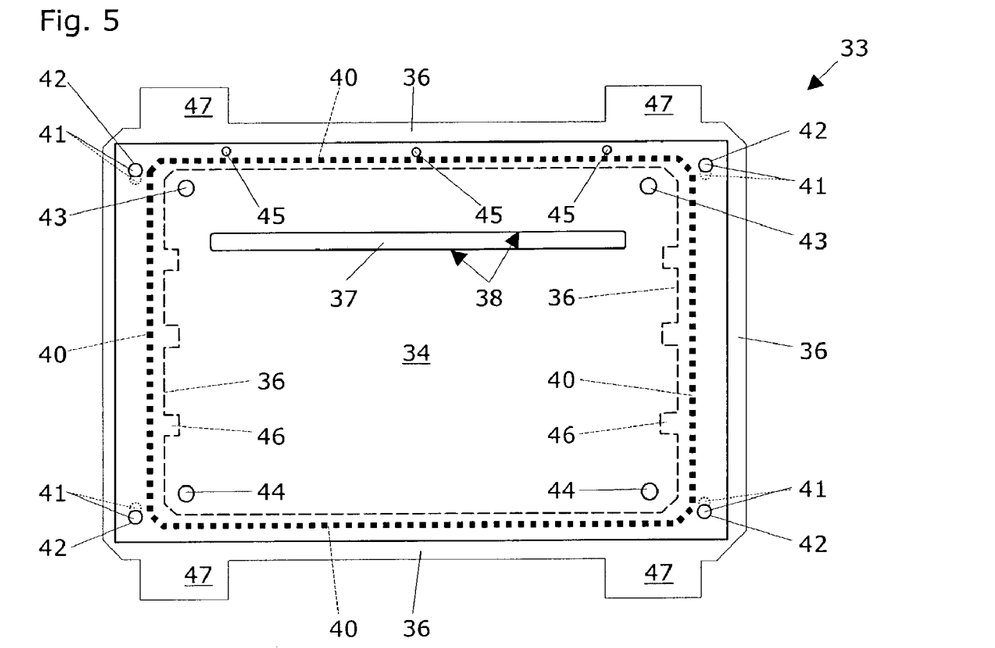
FIG. 5 shows a top view of the front plate of an assembled SDS-PAGE cassette according to a first embodiment, before the insertion of a strip holder.

FIG. 5 shows a top view of front plate 34 of an assembled SDS-PAGE cassette 33 according to a first embodiment, before the insertion of a strip holder 1. Recess 37 for inserting strip holder 1 is in the upper half of cassette 33, which is preferably used in this perpendicular position for the SDS-PAGE. Front plate 34 preferably has first openings 43 and/or second openings 44, positioned in the region of the space defined inside sealing edge 40, for ventilation or for introducing a gel, buffer, or stain. In addition, third openings 45 for introducing a separating medium are preferably positioned in the region of the space covered inside seal 36. This separating medium may be a gas (air, nitrogen, etc.) or a liquid (e.g. buffer) and is used for careful removal of the PAGE gel from plate 34, so that this surface of the PAGE gel may subsequently be subjected to a staining solution.

Seal 36 is essentially positionable in the region of the outer edge of plates 34, 35, includes annular, peripheral, elastically deformable sealing edge 40 described, and preferably projects all around plates 34, 35 over their outermost edge to protect plates 34, 35, which are preferably made of glass. Seal 36 is essentially implemented as flat, one-piece, and annular, it defines the interval between front plate 34 and back plate 35 and preferably has an elasticity which essentially corresponds to that of an SDS gel, the toughness of the seal, however, being greater than that of the gel. For a close connection between seal and SDS-PAGE gel, seal 36 has clips 46 to be polymerized into such a gel. The seal is therefore used as a frame for holding the gel, which must never be touched directly. For grasping the seal using a tool and/or a robot, it preferably has holding straps 47 on its outside. In the region outside its sealing edge 40, seal 36 includes attachment nubs 41 which are implemented to be snapped into corresponding holes 42 incorporated into both plates 34, 35.

A cassette 33 provisionally assembled (preferably by hand) includes a front plate 34, a back plate 35, and a seal 36, positioned between them and connecting both plates 34, 35. Such a cassette may also be transported with the aid of a robot, in that the robot grasps the holding straps using suitable means; for this purpose, seal 36 holds both plates 34, 35 together with sufficient security via its nubs 41.

Figure 6:
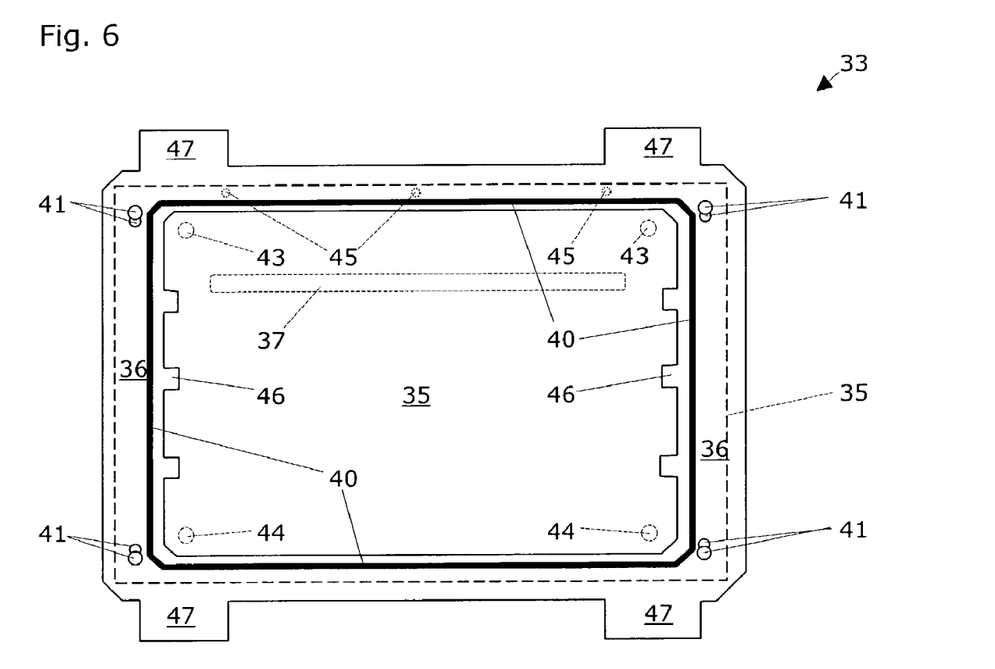
FIG. 6 shows a frontal view of an assembled SDS-PAGE cassette according to a first embodiment, with the front plate removed.

FIG. 6 shows a frontal view of an assembled SDS-PAGE cassette 33 according to the first embodiment, with the front plate removed; recess 37 and first openings 43 and/or second openings 44 of front plate 34 are only indicated with dashes. In addition, third openings 45 for introducing a separating medium are preferably positioned in the region of the space covered inside seal 36. This separating medium may be a gas (air, nitrogen, etc.) or a liquid (e.g. buffer) and is used for careful removal of the PAGE gel from back plate 35, so that this surface of the PAGE gel may subsequently be subjected to, for example, a staining solution.

The second part (second dimension) of a 2-D gel electrophoresis method using strip holder 1 and/or cassette 33 according to the present invention preferably runs as follows:

Two plates 34, 35 and a seal 36 are provisionally attached to one another by hand, by snapping attachment nubs 41 of the seal in holes 42 of the plates provided for them, and positioned in relation to one another.

Figure 7:
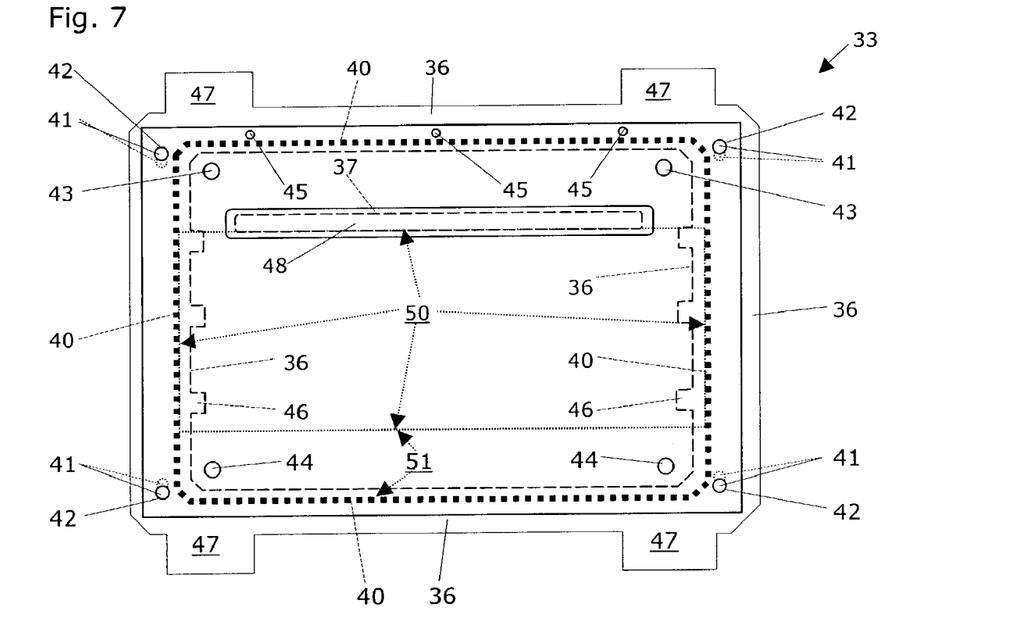
FIG. 7 shows a top view of the front plate of an assembled SDS-PAGE cassette according to a first embodiment, during casting of the SDS gel.

A gel comb 48 is inserted into recess 37 of front plate 34 of an SDS-PAGE cassette 33 and forms a seal in relation to inner surface 38 of recess 37. As an alternative to this, a blank cover (not shown) may be inserted into recess 37 to form a seal.

Cassette 33 is placed between two plate-shaped heating/cooling elements and/or temperature control walls (not shown), which form planar contacts with plates 34, 35, and is held upright transversely as shown in FIG. 7.

In this position of cassette 33, inserted gel comb 48 defines the upper edge of the SDS gel to be cast, at least in the region of IEF gel strip 3, to be inserted later.

Alternatively to this, propanol, butanol, and/or another liquid which is not miscible with the SDS gel and whose specific weight is lighter (and which therefore floats on the SDS gel), which fills the space 49 between plates 34, 35 and sealing edges 40 for at least a few millimeters, is introduced into space 49 via a first opening 43 after the casting of SDS gel 50. At the same time, excess gas present in space 49 escapes from other first opening 43. As an alternative to gel comb 48, this floating liquid also defines the upper edge of the SDS gel to be cast.

A desired casting temperature is now set via the temperature control walls (not shown), which form planar contacts. This casting temperature is preferably 37° C. A partial vacuum is preferably achieved between the heating/cooling elements and the plates via suction openings (not shown) in the heating/cooling elements, which improves the contact, and therefore the thermal transfer, between the plates and the temperature control walls even more. Liquid SDS gel 50 is now poured into space 49 between plates 34, 35 via second openings 44 until the upper edge of gel 50 touches gel comb 48 and/or until the position of the desired phase boundary SDS gel/floating liquid reaches this level. The excess gas in space 49 again escapes via openings 43 at the same time. Using a defined volume of glycerin 51 and/or another liquid, which is not miscible with SDS gel 50 and has a higher specific weight (and therefore forms a layer below the gel), a first buffer volume 53 is defined simultaneously.

SDS gel 50 is also cross-linked at a preferred polymerization temperature of 37° C. In this case, the partial vacuum between plates 34, 35 and the temperature control walls prevents the plates from deforming in accordance with the contraction of the polymerizing gel. Subsequently, gel comb 48 and/or the floating liquid and the blank cover are removed and strip holder 1 having IEF gel strip 3 of the first dimension is inserted into recess 37 to form a seal.

Figure 8:
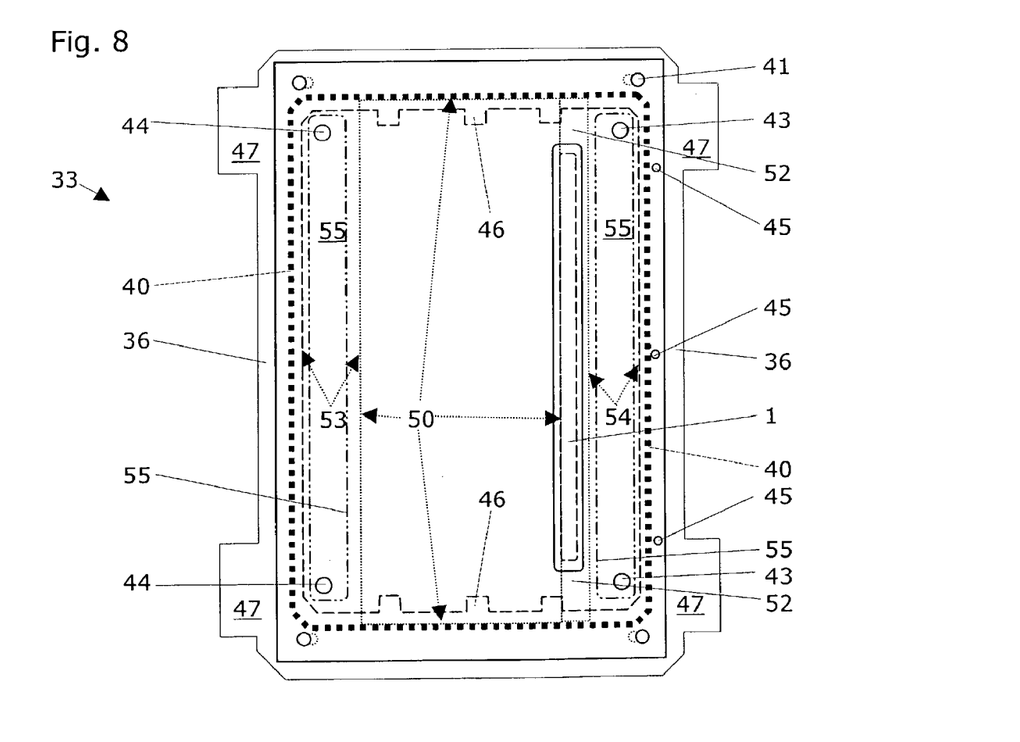
FIG. 8 shows a top view of the front plate of an assembled SDS-PAGE cassette according to a first embodiment after the insertion of a strip holder and casting using a contact gel, during performance of the SDS-PAGE.

A defined volume of contact gel 52 (preferably agarose) is added via one of first openings 43 until it completely encloses IEF gel strip 3 and is bonded to the SDS gel. At the same time, excess gas escapes from space 49 via other first opening 43 and space 49 between the plates is not completely filled, so that a second buffer volume 54 is formed. The contact gel is also polymerized completely.

Cassette 33 is now rotated by approximately 90°, so that—as illustrated in FIG. 8—it stands at least essentially upright lengthwise. Both buffer volumes 53, 54 are now rinsed with buffer.

Using a high-voltage control, a potential is applied via the two buffer lines or by contacts with additional electrically conductive layers 55 provided inside both buffer volumes 53, 54 and the electrophoresis is completed in the second dimension—preferably at a temperature of 20° C. The buffer for each pole may be connected to a circulation device for temperature control and filtration of the buffer (not shown) at the same time. Thanks to the preferred position of the cassette, standing upright lengthwise (cf. FIG. 8), during the SDS-PAGE, gas bubbles which may form in the buffer solutions are conveyed out of buffer volumes 53, 54 and may not influence the electrophoresis.

Via third openings 45, a separating medium, a gas (air, nitrogen, etc.) or a liquid (e.g. buffer), is introduced between back plate 35 and seal 36 and/or SDS gel 50, so that the PAGE gel carefully detaches from plate 35. At the same time, plate 35 is held by temperature control wall behind it using a partial vacuum. The remainder of cassette 33 (gel 50, seal 36, and front plate 34) is also held by the corresponding temperature control wall using a partial vacuum. The temperature control walls are preferably moved away from one another linearly and a frame (not shown) is introduced into the space arising between them. The temperature control walls, with the cassette parts adhering to them, are now moved toward one another again until the frame presses tightly against back plate 35 and seal 36 and defines a first staining space. A staining solution for displaying the separated proteins may now be introduced via third openings 45 or first or second openings 43, 44, which are provided in any case, into the first staining area, and the back surface of the SDS gel may be exposed at the same time.

As an alternative to the production of a staining space just described, seal 36 may be inflatable so that a staining space may also be produced on one or both sides of SDS gel 50 via synchronized inflation of elastic seal 36, introduction of a separating medium, and movement of one or both temperature control walls away from one another.

If desired, a second staining space between SDS gel 50 and plate 34 may be provided in a second, similar step and this front surface of gel 50 may also be exposed to the staining solution.

As an alternative to using a frame, both plates 34, 35 may also be sequentially replaced with others having suitable geometry, i.e., plates 34, 35 having a frame already provided on them.

After the staining of the gel on one or both sides using solutions known per se, gel 50 is laid on a surface with seal 36 and preferably scanned in the transmitted light.

Alternatively to this, the stained or unstained gel may be subjected to further steps, e.g. blotting of the proteins on membranes.

The complete 2-D electrophoresis method (first and second dimension) is preferably performed, with or without staining and scanning of gels and/or analysis of the results, in a computer-controlled, automatic system.

FIG. 7 shows a top view of front plate 34 of an assembled SDS-PAGE cassette 33 according to the first embodiment, during casting of SDS gel 50. Recess 37 is sealed using a gel comb 48 or a blank cover. A free-flowing gel material 50 and a displacement liquid (e.g. glycerin 51) are introduced into cassette 33 via second openings 44 to define a first buffer volume 53. The excess gas present in space 49 escapes via first openings 43.

FIG. 8 shows a top view of front plate 34 of an assembled SDS-PAGE cassette 33 according to the first embodiment, after the insertion of a strip holder 1 and casting with a contact gel 52, during performance of the SDS-PAGE. To reduce a possible voltage drop in the two buffer volumes, the inner surfaces of both plates 34, 35 are preferably provided with an electrically conductive film 55. Such films 55 may include metal and be applied via PVD (physical vapor deposition, such as sputtering or vacuum evaporation) or CVD (chemical vapor deposition). Preferably, highly electrically conductive metals (such as gold or platinum) which are chemically inert are selected in this case. Chromium films are particularly suitable as bonding films between glass plates 34, 35 and the conductive films.

Figure 9:
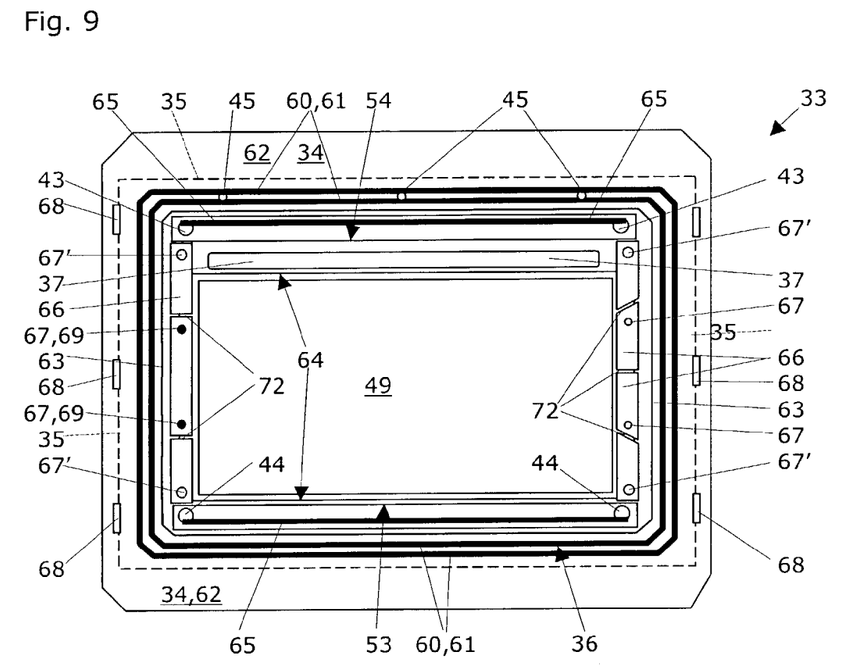
FIG. 9 shows a top view on the inside of the front plate of an assembled SDS-PAGE cassette according to a second embodiment, during casting of the SDS gel.

FIG. 9 shows a top view on the inside of the front plate 34 of an assembled SDS-PAGE cassette according to a second embodiment, during casting of the SDS gel. This second embodiment is characterized in that a seal 36 with one or two 0rings or sealing lips respectively is provided. These O-rings or sealing lips 60 preferably are made of Viton or a soft PVC. In the case that O-rings are used, the front plate 34 comprises one or two ring-like depressions 61 according to the O-rings, whereby these ring-like depressions 61 preferably are just so deep that the O-rings extend beyond the front plate 34 in their unloaded state. In an alternative embodiment, the single or double O-rings or sealing lips may be injection molded to the front plate 34, thereby reaching essentially the same geometrical conditions. Especially preferred is a front plate 34 with one ore several elevations 63 implemented for being abutted with the other plate 35. In this case, these elevations 63 define the measure of deformation of the seal 36 in their loaded state and therefore the final distance between the plates 34,35. A defined thickness of the PAGE gel results from this distance.

According to the invention, this defined distance between the plates 34,35 or the defined thickness of the gel respectively is reached by pressing the two plates 34,35 against each other. This pressing against each other may be achieved by a partial vacuum applied between the two O-rings or sealing lips 60 and/or through the exertion of a force onto the outside plane of the two plates 34,35. The exertion of a line-like force directed to the backside of the plate that carries the O-rings or sealing lips has proved its worth too. On one or on both sides of the gel space 49 that are running along the seal 36 and that adjoin at right angles to the buffer volumes 53,54, glass fiber stripes 66 are laid in between the plates and are at least partially polymerized into the gel. These glass fiber stripes 66 comprise holes 67,67'. Positioning pins 69 located on the front plate 34 engage with the corresponding holes 67 of the glass fiber stripes 66. Thus, the glass fiber stripe or stripes 66 are held in a defined position in relation to the front plate 34 and also in relation to the entire PAGE cassette 33. Take-off pins of a take-off cylinder may engage with the holes 67' (cf. FIG. 11).

Preferably, these glass fiber stripes 66 are made in two or more parts, in order to create one ore more dilatation gaps 72 running essentially across the glass fiber stripes. With the provision of such dilatation gaps 72, possibly occurring volume changes in the gels 50 may be compensated so that these gels may not be destroyed by too large deformations. Very narrow glass fiber stripes that are just able to take up the holes 67,67' are especially preferred; however, it is important that after the at least partial infiltration with gel material 50 and after the polymerization of the latter the holes 67,67' stay open. This way, reinforced holes 67,67' in the gels 50 are produced by the glass fiber stripes 66 finally.

Preferably with clips 68 that snap over an inlaid glass plate 35, the two plates 34,35 are held together provisionally. Preferably by the application of a partial vacuum via third openings 45 that are located between the O-rings or sealing lips 60 or by a pressing force, the plates 34,35 are brought to the final distance then.

Figure 10:
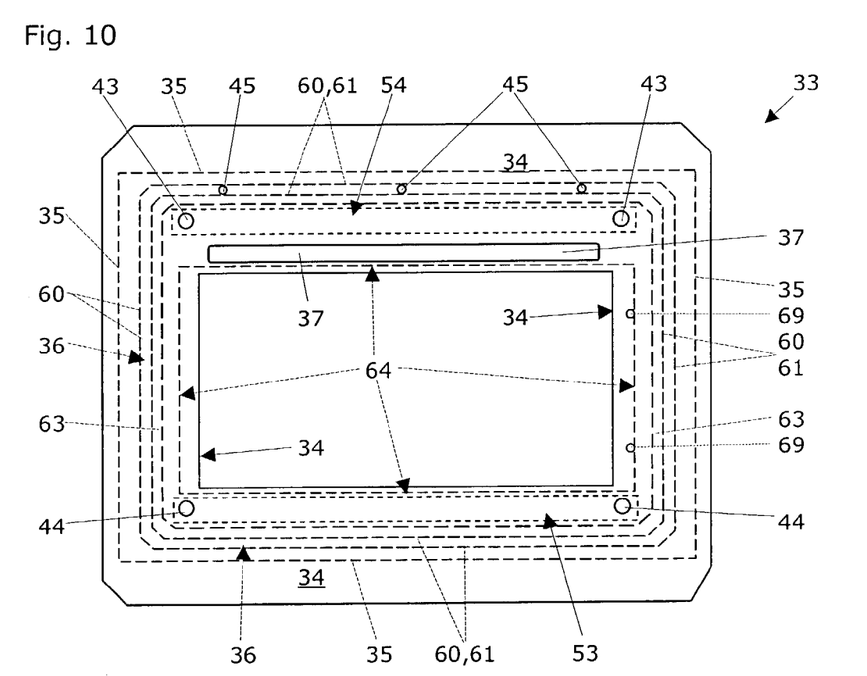
FIG. 10 shows a top view on the outside of the front plate of an assembled SDS-PAGE cassette according to a second embodiment, during casting of the SDS gel.

FIG. 10 shows a top view on the outside of the front plate 34 of an assembled SDS-PAGE cassette according to a second embodiment, during casting of the SDS gel. Both O-rings or sealing lips 60 of the seal 36 are drawn in broken lines as well as the outline of a relatively thin glass plate 64 which is glued into the front plate 34 or around which the synthetic material of the front plate is injection molded. As this front plate 34 may be built quite massive, it preferably comprises deeper and thereby larger first and second buffer volumes 53,54 that are drawn in broken lines as well. First and second openings 43,44 mouth into these buffer volumes 53,54 for introducing a gel, buffer, or stain, or for ventilation. In addition, electrode sticks 65 are preferably placed within these buffer volumes (cf. FIG. 9). These electrode sticks 65 later are surrounded by buffer and are connected via feeding lines with the high-voltage control. According to the second embodiment of the invention, also this front plate 34 of the gel electrophoresis cassette 33 comprises a recess 37. This recess 37 is adapted in it's size and shape to a strip holder 1 with a carrier surface 2. A gel strip 3 for the isoelectric focusing of molecules using gel electrophoresis is accommodated on this carrier surface 2. The strip holder 1 comprises a base plate 4 including at least one stop 5, which is offset to a lower level in relation to the carrier surface 2 and at least one sealing surface 6. This stop 5 is implemented to be applied to counter surfaces 7 of an electrophoresis chamber, i.e. an IEF chamber 15 or an SDS-PAGE cassette 33. By the offset of this stop 5 to a lover level in relation to the carrier surface 2, the installation depth of strip holder 1, which carries a gel strip 3, into this electrophoresis cassette 33 is determined. Thus, the strip holder 1 is insertable into this recess 37 in such a way that the stop 5 of the base plate 4 is applied to the outer surface of the front plate 34 and the sealing surface 6 presses tightly against the inner surface 38 of the recess 37.

Figure 11:
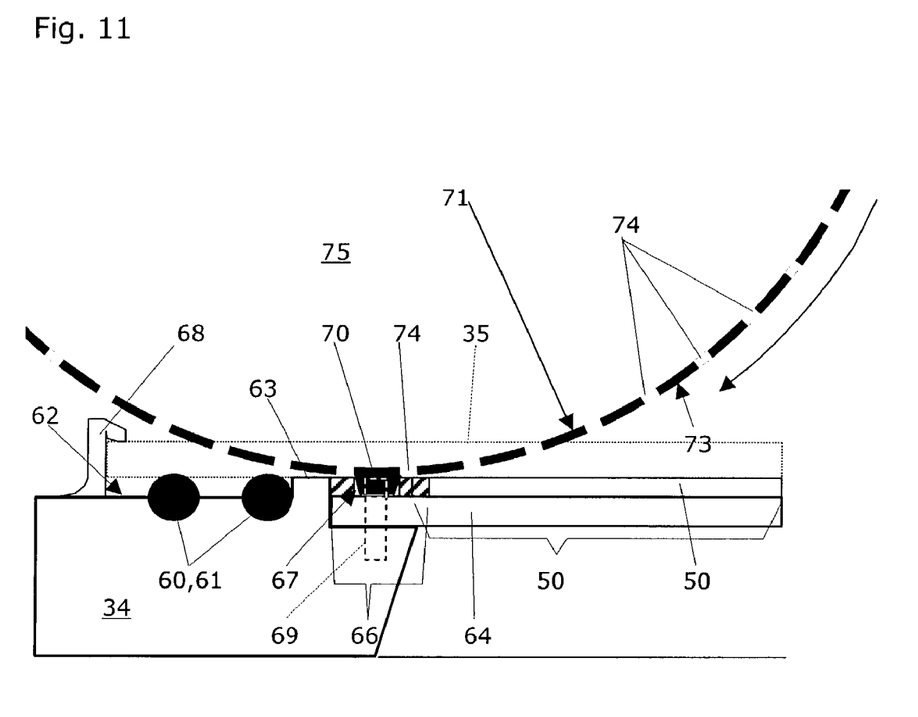
FIG. 11 shows a vertical cross section through an opened SDS-PAGE cassette according to a second embodiment, during taking off the SDS gel with a taking-off cylinder.

FIG. 11 shows a vertical cross section through an opened SDS-PAGE cassette according to a second embodiment, during taking off the SDS gel with a taking-off cylinder. After completing the electrophoresis, this taking-off an SDS-PAGE gel 50 becomes particularly necessary if the gel has to be stained from both sides. For taking-off the gel 50 from the relatively thin glass plate 64, a taking-off cylinder 71 with taking-off pins 70 is approached to the holes of the glass fiber stripes 66 polymerized into the gel until the taking-off pins 70 engage with these holes 67' corresponding in distance and dimension.

The taking-off cylinder 71 preferably comprises suction holes 74 situated on its surface 73 which are connected to a room 75 with reduced pressure located inside the take-off cylinder 71. This room 75 with reduced pressure preferably is connected to a suction pump via a suction line (not shown). After the positioning of the taking-off cylinder 71 at the gel 50 as just described, in the inside of the take-off cylinder a reduced pressure is produced. By the resulting suction, one or more polymerized in glass fiber stripes 66 together with an adjacent portion of the gel 50 are attracted and held on the take-off cylinder 71. Additional suction holes 74 may be distributed on a larger area of the take-off cylinder 71 for holding the gel 50. Subsequently, the SDS gel is taken up onto the turning cylinder and this way transferred to a staining bath (not shown).

In the staining bath, the gel is left gliding off from the taking-off cylinder by turning the latter. Preferably this is executed by engaging the reinforced holes 67 of the gel 50 with positioning pins located in the staining bath. Thus, the stained gel may be taken off the staining bath in a defined way (similar to the taking-off from the glass plate 64) and by an automatic and then be transferred to an analysis apparatus (not shown).

Notwithstanding the figures shown, parts of IEF chamber 15 (e.g. base plate 4 having lip seal 11 or O-ring 13; frame 16 having cover 20) and/or SDS-PAGE cassette 33 may be combined into functional units which are produced in one piece. The reference numbers refer to the same features in each case, even if all features are not expressly described for every figure.

What is claimed is:

1. A gel electrophoresis cassette, which includes two plates and at least one seal separating the plates, the seal being implemented as a one-piece, annular seal and positioned in a region of an outer edge of the plates, one of the plates comprising in an area within the annular seal a recess extending through the one of the plates, wherein the size and shape of the recess is adapted to receive a strip holder with a base plate comprising a carrier surface for accommodating a gel strip for isoelectric focusing of molecules using gel electrophoresis, the base plate including at least one stop which is offset to a lower level in relation to the carrier surface and at least one sealing surface, the stop being configured to be applied to counter surfaces of an electrophoresis chamber, wherein by offsetting the stop to a lower level in relation to the carrier surface, the installation depth of the strip holder, which carries a gel strip, into the electrophoresis cassette is determined, wherein the strip holder is insertable into the recess in such a way that the stop of the base plate is applied to an outer surface of the plate with the recess, and wherein the sealing surface presses tightly against an inner surface of the recess.

2. The cassette according to claim 1,
wherein the seal is implemented as a flat seal and includes a peripheral, annular, elastically deformable sealing edge on both of the sides which press against the plates.

3. The cassette according to claim 1,
wherein the seal is implemented as an O-ring seal with one or two O-rings.

4. The cassette according to claim 1,
wherein the seal is implemented as a lip seal with one or two sealing lips.

5. The cassette according to one of the claims 2, 3 or 4, wherein at least one of the two plates has elevations implemented for being abutted by the other plate, the elevations defining the deformation of the seal and the distance between the plates.

6. The cassette according to claim 1,
wherein at least one of the plates includes first openings and/or second openings, appropriately positioned in the area inside the annular seal, for ventilation or for introducing a gel, buffer, or stain.

7. The cassette according to claim 6,
wherein at least one of the plates includes third openings, appropriately positioned in the area inside the annular seal, for introducing a separating medium or for applying a partial vacuum.

8. A system for performing 2-D gel electrophoresis, which comprises a working platform for arranging one or more gel electrophoresis cassettes according to claim 1 for performing gel electrophoresis.

9. The system according to claim 8,
further comprising one or more chambers for isoelectric focusing of molecules in gel strips, whereby each one of the chambers comprises:
a strip holder insertable into a recess in one of the plates of a gel electrophoresis cassette; and
a frame having a peripheral wall and an upper and lower counter surface,
the strip holder being insertable into the frame in such a way that at least one stop is applied to the lower counter surface and the sealing surface presses tightly against an inner surface of the wall.

10. The system according to claim 8 or 9,
which comprises a temperature control device for the gel electrophoresis cassettes and/or chambers for isoelectric focusing of molecules in gel strips.

11. The system according to claim 10,
wherein the temperature control device for the gel electrophoresis cassettes comprises at least one temperature control wall which controls the temperature of a SDS gel during polymerization and/or during electrophoresis via a planar contact with the plates of each cassette, and
wherein the temperature control device includes two temperature control walls which accommodate one cassette between the control walls, and
wherein each control wall includes suction openings directed toward the respective plates of the cassette.

12. The system according to claim 9,
which comprises a robot arm for transferring individual parts of the chambers and/or cassettes to and from the chambers for isoelectric focusing of molecules in gel strips and/or the gel electrophoresis cassettes, a computer for controlling the robot, a single-channel high-voltage control for individual control of the chambers for isoelectric focusing of molecules in gel strips, and a display screen.

13. A 2-D gel electrophoresis method, in which
a dehydrated gel strip is positioned on a carrier surface of a base plate of a strip holder, the base plate comprising at least one stop offset to a lower level in relation to the carrier surface and at least one sealing surface, the strip holder being insertable into a frame of an IEF-chamber, the frame having a periphery wall and an upper and lower counter surface, the stop being configured to be applied to the lower counter surface, and the sealing surface being configured to press tightly against an inner surface of the wall;
a sample is applied to the gel strip and the IEF-chamber is closed with a cover that is applied to the upper counter surface of the frame, the cover includes two electrode holders movably inserted into the cover;
said electrode holders are inserted in an upper or lower level, through which one electrode at a time, which are each restrictedly movable perpendicular to the surface of the gel strip lying on the carrier surface of the strip holder, is positioned at an interval to the surface of the gel strip or comes into contact with the gel strip;
said gel strip and the sample both on said strip holder are subjected to electrical high voltage via the electrodes until isoelectric focusing of molecules in the gel strip has occurred, the temperature of the gel strip being controlled using a temperature control device;
wherein said strip holder with the gel strip is applied to counter surfaces of a gel electrophoresis cassette according to claim 1, and wherein by offsetting the stop to a lower level in relation to the carrier surface, the installation depth of the strip holder, which carries the gel strip, in the gel electrophoresis cassette is determined.

14. The method according to claim 13,
wherein in the isoelectric focusing step the electrical high-voltage is generated using a single-channel control device, which regulates electrical current parameters and, stores the parameters for subsequent use and/or display.

15. The method according to claim 13,
wherein the gel electrophoresis cassette is positioned between two temperature control walls of a system for performing 2-D gel electrophoresis, the walls being applied to the cassette in such a way that the annular seal between the plates of the cassette is elastically deformed, and the distance between the plates of the cassette being essentially defined by elevations on one of the plates implemented to abut the other plate, and
wherein a partial vacuum is produced between each plate of the cassette and each temperature control wall via suction openings disposed on the temperature control wall.

16. The method according to claim 15,
wherein the recess is sealed using a gel comb or a blank cover, and wherein, while using a blank cover, a means for defining a straight casting edge of the gel material to be cast is put into the cassette and a free-flowing gel material and a displacement liquid, which is not miscible with the gel material, are introduced into the cassette via second openings provided on one of the plates to define a first buffer volume.

17. The method according to claim 16,
wherein glass fiber stripes with holes are laid between the plates of the cassette, and wherein the glass fiber stripes are at least partially polymerized into the gel material.

18. The method according to claim 17,
wherein the gel material is polymerized in the cassette under controlled temperature conditions, and—if present—the means for defining a straight casting edge in the gel material and the displacement liquid are removed from the cassette, a strip holder having the gel strip is sealingly inserted into the recess, and—while forming a second buffer volume—a contact gel for producing contact of the gel strip with the gel material is introduced into the cassette via first openings and polymerized.

19. The method according to claim 18,
wherein the first and second buffer volumes are essentially filled with buffer solution via the second and first openings, the buffer volumes are each connected to a pole of a high-voltage source, and SDS gel electrophoresis is performed under controlled temperature conditions.

20. The method according to claim 19,
wherein the SDS gel electrophoresis is performed in a position of the cassette standing upright lengthwise.

21. The method according to claim 19,
wherein, for staining and/or scanning the gel material, a separating medium is introduced via third openings provided in at least one plate of the cassette, and
one or both plates of the cassette are separated from the gel material and the annular seal, after which one or both exposed surfaces of the gel material are exposed to a staining solution and aligned in relation to a scanning device after the staining step.

22. The method according to claim 21,
further comprising lifting the gel material off one of the plates with a taking-off cylinder, comprising the steps of:
moving take-off pins of the taking-off cylinder toward the holes of the glass fiber stripes that are polymerized into the gel material until the taking-off pins engage with the holes in the glass fiber stripes, and
picking up the gel material with the rotating take-off cylinder.

23. The method according to claim 22,
wherein the taking-off cylinder comprises suction holes situated on a surface thereof, wherein at least one or more glass fiber stripes polymerized into the gel material are attracted together with an adjacent portion of the gel material and are held on the take-off cylinder.

24. The method according to claim 16,
wherein the seal comprises clips, and
wherein the clips are arranged between the plates of the cassette and polymerized into the gel material.

25. The method according to claim 13,
wherein all method steps are automatically performed in a system for performing 2-D gel electrophoresis, which comprises a working platform for arranging one or more gel electrophoresis cassettes according to claim 1 for performing SDS-PAGE gel electrophoresis.

* * * * *